United States Patent [19]

Warnant et al.

[11] 4,186,128
[45] Jan. 29, 1980

[54] NOVEL PROCESS FOR THE PREPARATION OF 3-OXIMES OF STEROIDS

[75] Inventors: Julien Warnant, Neuilly-sur-Seine; Jean Jolly, Fontenay-sous-Bois, both of France

[73] Assignee: Roussel UCLAF, Paris, France

[21] Appl. No.: 926,865

[22] Filed: Jul. 24, 1978

[30] Foreign Application Priority Data

Aug. 31, 1977 [FR] France .................................. 77 26432

[51] Int. Cl.² ................................................ C07J 1/00
[52] U.S. Cl. ............................... 260/239.5; 260/397.5; 260/343.42
[58] Field of Search ............... 260/586 H, 239.5, 397.5

[56] References Cited
U.S. PATENT DOCUMENTS 3,341,557  9/1967  Babcock et al. .................. 260/397.3

Primary Examiner—Elbert L. Roberts
Attorney, Agent, or Firm—Hammond & Littell

[57] ABSTRACT

A novel process for the preparation of 3-oximes of the formula

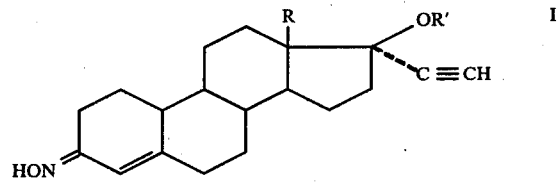

wherein R is selected from the group consisting of methyl and ethyl and R' is selected from the group consisting of hydrogen and acyl of an organic carboxylic acid of 2 to 8 carbon atoms and novel intermediates formed therein.

7 Claims, No Drawings

NOVEL PROCESS FOR THE PREPARATION OF 3-OXIMES OF STEROIDS

STATE OF THE ART

The preparation of 3-oximes of steroids is described in Steroids, Vol. 23 (1), 1974, p. 49–64 and in French Pat. No. 1,490,590.

OBJECTS OF THE INVENTION

It is an object of the invention to provide a novel process for the preparation of the 3-oximino-steroids of formula I.

It is a further object of the invention to provide novel intermediate products formed in the process.

These and other objects and advantages of the invention will become obvious from the following detailed description.

THE INVENTION

The novel process of the invention for the 3-oximines of the formula

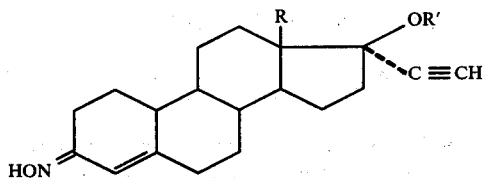

wherein R is selected from the group consisting of methyl and ethyl and R' is selected from the group consisting of hydrogen and acyl of an organic carboxylic acid of 2 to 8 carbon atoms comprises reacting a compound of the formula

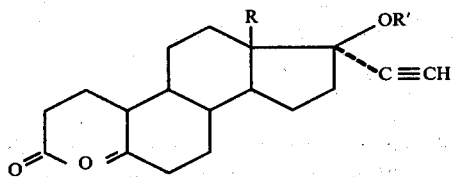

wherein R and R' have the above definition with a secondary amine and then with an acid and finally with hydroxylamine or a salt thereof to obtain the corresponding compound of formula I in the form of a mixture of syn and anti isomers which, if desired, can be separated into individual isomers by known methods such as chromatography.

Examples of suitable organic carboxylic acids are alkanoic acids such as acetic acid, propionic acid, butyric acid, heptanoic acid and caproic acid with acetic acid being preferred.

The compounds of formula I are known products which have been prepared by other processes such as that described in U.S. Pat. No. 3,532,689. The process of the invention permits the total synthesis of the products of formula I in a surprising manner and with excellent yields.

The process of the invention is especially useful to produce the compounds of formula I wherein R is ethyl and those wherein R' is acetyl.

The process of the invention is preferably effected under anhydrous conditions and the enamine formed by the reaction of the secondary amine and the compound of formula II may be isolated or not as the process proceeds well either way. The preferred secondary amines are pyrrolidine or morpholine and the preferred acids are acetic acid or phosphoric acid although other secondary amines and acids are equally useful.

The compounds of formula II which are the starting materials are generally known compounds and may be prepared by the process of French Pat. No. 1,490,590.

Among the novel intermediate compounds of the invention are 3-pyrrolidyl-13β-ethyl-17β-acetoxy-17α-ethynyl-Δ3,5-gonadiene, 3,5-bisethylenedioxy-4,5-seco-13β-ethyl-17β-acetoxy-17α-ethynyl-gonane and 4,5-seco-13β-ethyl-17β-acetoxy-17α-ethynyl-gonane-3,5-dione. The latter product may be prepared by reacting 3,5-bisethylenedioxy-4,5-seco-13β-ethyl-17α-ethynyl-gonane-17β-ol (described in Israel Pat. No. 28,020) with acetic anhydride to form 3,5-bisethylenedioxy-4,5-seco-13β-ethyl-17β-acetoxy-17α-ethynyl-gonane which is then hydrolyzed to the desired product.

The process of the invention permits the direct passage from an enamine such as 3-pyrrolidyl-13β-ethyl-17β-acetoxy-17α-ethynyl-Δ3,5-gonadiene to the corresponding 3-oximino compound. 3-oximino steroids are classically prepared starting from the corresponding ketones and the 3-ketones starting from the enamines. To pass directly from an enamine conjugated to the corresponding oxime without the intermediate formation of a 3-keto-Δ4-derivative has never been realized until now. Chromatographic analysis affirms that there is never formation of the 3-keto-Δ4 compound. The reaction may be explained by the first formation of an immonium salt by action of the acid with the enamine followed by reaction of the immonium salt with hydroxylamine to form the oxime by the following reaction scheme.

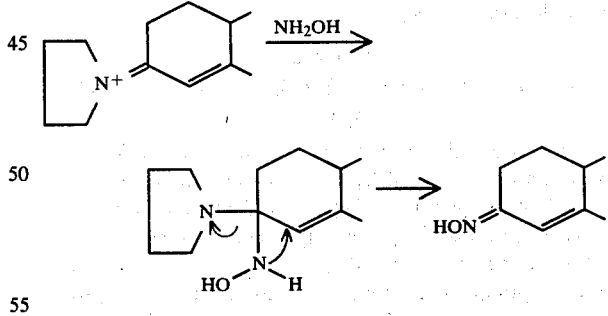

The process of the invention gives excellent yields on an industrial scale with the final product being almost totally free of impurities. For example, 3-oximino-13β-ethyl-17β-acetoxy-17α-ethynyl-Δ4-gonene-3-one is prepared with a yield greater than 83% starting from 4,5-seco-13β-ethyl-17β-acetoxy-17α-ethynyl-gonane-3,5-dione.

In the following examples there are described several preferred embodiments to illustrate the invention. However, it should be understood that the invention is not intended to be limited to the specific embodiments.

EXAMPLE 1

3-oximino-13β-ethyl-17β-acetoxy-17α-ethynyl-Δ⁴-gonene

STEP A:
3,5-bisethylenedioxy-4,5-seco-13β-ethyl-17β-acetoxy-17α-ethynyl-gonane A suspension of 58 g of 3,5-bisethylenedioxy-4,5-seco-13β-ethyl-17α-ethynyl-gonane-17β-ol (prepared by process of Israel Pat. No. 28,020) in 174 ml of toluene was heated to reflux with stirring and nitrogen bubbling therethrough while distilling 58 ml of toluene therefrom and then 116 ml of acetic anhydride were added thereto. The mixture was then heated to reflux and treated to recover 3,5-bis-ethylenedioxy-4,5-seco-13β-ethyl-17β-acetoxy-17α-ethynyl-gonane melting at 165°–166° C.

STEP B:
4,5-seco-13β-ethyl-17β-acetoxy-17α-ethynyl-gonane-3,5-dione 116 ml of water were added to the acetic acid solution of Step A and the mixture was refluxed for 3 hours with toluene distillation. The mixture was vacuum filtered and the recovered precipitate was washed and dried to obtain 51.35 g of 4,5-seco-13β-ethyl-17β-acetoxy-17α-ethynyl-gonane-3,5-dione melting at 123° C.

STEP C:
3-pyrrolidyl-13β-ethyl-17β-acetoxy-17α-ethynyl-Δ³,⁵-gonadiene 15 ml of pyrrolidine were added to a mixture of 30 g of the product of Step B in 150 ml of methanol and the mixture was stirred for one hour at 25 to 30° C. under a nitrogen atmosphere. The mixture was vacuum filtered and the recovered product was washed and dried to obtain 35 g of 3-pyrrolidyl-13β-ethyl-17β-acetoxy-17α-ethynyl-Δ³,⁵-gonadiene melting at 153° C. and having a specific rotation of $[\alpha]_D^{20} = -276° \pm 3°$ (c=0.5% in dimethylformamide).

STEP D:
3-oximino-13β-ethyl-17β-acetoxy-17α-ethynyl-Δ⁴-gonene 1.931 g of anhydrous sodium acetate were added to a solution of 1.534 g of hydroxylamine hydrochloride in 60 ml of methanol to obtain a hydroxylamine suspension. A mixture of 6 g of the product of Step C in 12 ml of acetic acid was stirred under a nitrogen atmosphere for 30 minutes and was then poured into the hydroxylamine suspension. The mixture was refluxed with stirring and nitrogen bubbling therethrough for 3 hours and after cooling to 20° C., 180 ml of water were added to the mixture. The mixture was iced and vacuum filtered and the recovered precipitate was washed and empasted with water to obtain 5.327 g of product. The latter was crystallized from methanol to obtain 4.795g of 3-oximino-13β-ethyl-17β-acetoxy-17α-ethynyl-Δ⁴-gonene melting at 223° C. and having a specific rotation of $[\alpha]_D^{20} = 40$ to 46° (c=0.5% in chloroform).

EXAMPLE 2

3-oximino-17α-ethynyl-Δ⁴-estrene-17β-ol-3-one

Using the procedure of Step C of Example 1, 4,5-seco-17α-ethynyl-estrane-17β-ol-3,5-dione was reacted to obtain 3-pyrrolidyl-17α-ethynyl-Δ³,⁵⁽⁶⁾-estradiene-17β-ol melting at 186° C.

Using the procedure of Step D of Example 1, the latter product was reacted to obtain 3-oximino-17α-ethynyl-Δ⁴-estrene-17β-ol-3-one melting at 112°–114° C.

Various modifications of the process and intermediate of the invention may be made without departing from the spirit or scope thereof and it is to be understood that the invention is intended to be limited only as defined in the appended claims.

We claim:

1. A process for the preparation of 3-oximes of the formula

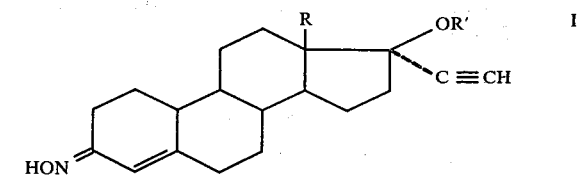

wherein R is selected from the group consisting of methyl and ethyl and R' is selected from the group consisting of hydrogen and acyl of an organic carboxylic acid of 2 to 8 carbon atoms comprising reacting a compound of the formula

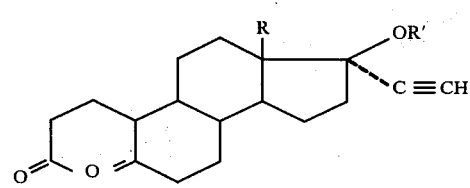

wherein R and R' have the above definition with a secondary amine selected from the group consisting of pyrrolidine and morpholine to form the corresponding 3-pyrrolidyl or 3-morpholinyl-17α-ethynyl-Δ⁴-gonene and then reacting the latter which has been isolated or not isolated, with an acid and finally with hydroxylamine or a salt thereof to obtain the corresponding compound of formula I in the form of a mixture of syn and anti isomers which, if desired, can be separated into individual isomers.

2. The process of claim 1 wherein R is ethyl.

3. The process of claim 1 wherein R' is an acyl of an organic carboxylic acid of 2 to 8 carbon atoms.

4. The process of claim 1 wherein R' is acetyl.

5. The process of claim 2 wherein R' is acetyl.

6. The process of claim 1 wherein the reaction is effected under anhydrous conditions.

7. A compound selected from the group consisting of 3-pyrrolidyl-13β-ethyl-17β-acetoxy-17α-ethynyl-Δ³,⁵-gonadiene, 3,5-bisethylenedioxy-4,5-seco-13β-ethyl-17β-acetoxy-17α-ethynyl-gonane and 4,5-seco-13β-ethyl-17β-acetoxy-17α-ethynyl-gonane-3,5-dione.

* * * * *